United States Patent [19]

Lang

[11] Patent Number: 5,006,345
[45] Date of Patent: Apr. 9, 1991

[54] DIRECT TABLETING AUXILIARY

[75] Inventor: Siegfried Lang, Ludwigshafen, Fed. Rep. of Germany

[73] Assignee: BASF Aktiengesellschaft, Fed. Rep. of Germany

[21] Appl. No.: 284,765

[22] Filed: Dec. 12, 1988

Related U.S. Application Data

[63] Continuation of Ser. No. 826,094, Feb. 6, 1986, abandoned.

[30] Foreign Application Priority Data

Feb. 16, 1985 [DE] Fed. Rep. of Germany ....... 3505433

[51] Int. Cl.$^5$ ................................................ A61K 9/26
[52] U.S. Cl. ..................................... 424/467; 424/489; 427/3
[58] Field of Search .................... 424/489, 467, 486; 427/3

[56] References Cited

U.S. PATENT DOCUMENTS 4,353,887 10/1982 Hess et al. ............................ 424/467
4,681,755 7/1987 Colombo et al. .................... 424/486

FOREIGN PATENT DOCUMENTS 2126810 12/1971 Fed. Rep. of Germany ...... 424/486
3012136 2/1984 Fed. Rep. of Germany .
908016 10/1962 United Kingdom ................ 424/486
1391554 4/1975 United Kingdom ................ 424/486

OTHER PUBLICATIONS

Kornblum et al. (1973) Journal of Pharmaceutical Sciences 62 (1):43–49.
Kamp et al. (1983) Pharmaceutisch Weekblad Scientific Edition 5:165–171.
Voight (1975) Lehrbuch der pharmazutischen Technologie, p. 188, Section 8.5.9.
Pharmacopoea Danica (1948) 9th Edition, p. 82.

Primary Examiner—Thurman K. Page
Attorney, Agent, or Firm—Keil & Weinkauf

[57] ABSTRACT

Direct tableting auxiliaries essentially consists of
(A) from 88 to 96% by weight of pulverulent carrier conventionally used for the preparation of tablets and consisting of lactose, or lactose together with not more than the same amount of another carrier,
(B) from 2 to 6% by weight of polyvinylpyrrolidone having a K value of from 20 to 40, and
(C) from 2 to 10% by weight of crosslinked, insoluble polyvinylpyrrolidone, all percentages being based on the direct tableting auxiliary, and are obtained by spray drying, spray granulation or wet granulation.

The novel direct tableting auxiliaries exhibit good flow and good compressibility under low pressure, and the tablets produced using the said auxiliaries possess excellent disintegration properties coupled with great hardness and low abrasion.

16 Claims, No Drawings

DIRECT TABLETING AUXILIARY

This application is a continuation of application Ser. No. 826,094, filed on Feb. 6, 1986 now abandoned.

The present invention relates to a direct tableting auxiliary based on lactose powder mixed intimately with a binder, preferably polyvinylpyrrolidone, and a tablet disintegrating agent, preferably crosslinked insoluble polyvinylpyrrolidone.

A large number of carriers, such as microcrystalline cellulose, cellulose, dicalcium phosphate, sorbitol, and in particular lactose, are widely used in the pharmaceutical industry for tablet production.

The carriers used should meet a large number of requirements, some of which are contradictory; examples are good flow properties, good compressibility under low pressure, great hardness and abrasion resistance and a tendency to disintegrate readily after intake.

These requirements are met to a greater or lesser extent by commercial tableting auxiliaries. Hence, the further auxiliaries are incorporated during tableting, eg. lubricants, binders and disintegrators for disintegrating the tablet on contact with gastric juice.

Particularly where lactose is used as a tableting auxiliary, some users adopt a procedure in which lactose powder is mixed with the active compound to be administered, if necessary together with the disintegrator, eg. crosslinked polyvinylpyrrolidone, an aqueous solution of a binder, eg. polyvinylpyrrolidone, is sprayed onto the mixture, the resulting moist powder is dried, a lubricant is added and the mixture is then pressed to give tablets.

This method too, which gives very good results, does not fully meet all of the stated requirements. Moreover, the procedure described is complicated and labor-intensive and requires the use of organic solvents for water-sensitive active compounds.

It is an object of the present invention to provide a tableting auxiliary which not only meets the stated requirements but, after being mixed with the active compound, also permits tablets to be produced directly and furthermore makes it possible to reduce the amount of tableting auxiliary.

We have found that this object is achieved, according to the invention, by a direct tableting auxiliary (ie. an auxiliary which is free of active compounds) which consists essentially (ie. the direct tableting auxiliary may contain only small amounts, eg. up to 5% by weight, of further substances) of an intimate mixture of (A) from 88 to 96, preferably from 90 to 94, % by weight of a pulverulent carrier which is conventionally used for the production of tablets and consists of lactose or of lactose together with not more than the same amounts of other carriers, (B) from 2 to 6, preferably from 2 to 5, % by weight of a binder selected from the group consisting of hydroxypropylmethylcellulose, hydroxypropylcellulose, gelatine and, preferably, polyvinylpyrrolidone having a K value of from 20 to 40, and (C) from 2 to 10, preferably from 3 to 6, % by weight of a tablet disintegrating agent selected from the group consisting of crosslinked carboxymethylcellulose, crosslinked carboxymethyl starch, formaldehyde casein and, preferably, crosslinked, insoluble polyvinylpyrrolidone, all percentages being based on the direct tableting auxiliary.

In a preferred embodiment of the invention, lactose alone, eg. lactose EP (EP =European Pharmacopoeia) monohydrate having a particle size less than 600 μm is used as the carrier. However, it is also possible to use, for example, mixtures of lactose and mannitol or of lactose and calcium phosphate.

Suitable binders (B) are hydroxypropylmethylcellulose as available under the tradenames PHARMACOAT ® from Shinetsu, Japan (type A, USP XXI) or METHOCEL ® from Dow Chemical (type B), hydroxypropylcellulose, eg. KLUCEL ® LF from Hercules, USA, gelatin NF XVI and, preferably, polyvinylpyrrolidone having a K value of from 20 to 40, preferably from 28 to 32, the last-mentioned substance being described in, for example, R. Vieweg, M. Reiher and H. Scheurlen, Kunststoff-Handbuch 1971, Volume 11, page 558, Munich: Hanser or Ullmann, 4th edition, Volume 19, pages 385–386. For the definition of the K value, reference may be made to the Povidone Monograph, USP XXI, 1985. These publications are therefore hereby incorporated by reference.

The tablet disintegrating agent (C) is selected from the group consisting of sodium carboxymethyl starch, obtainable as PRIMOJEL ® from Scholrten, NL or EXPLOTAB ® from Mendell, USA (cf. also R.F. Shangraw, Drug, Gosm. Ind. 122, No. 68 and 123, No. 1, 34 (1978), crosslinked carboxymethylcellulose, eg. sodium carboxymethylcellulose USP XXI (croscarmellose sodium), obtainable as NYMZEL ® ZSB 16 from Nyma, Netherlands, and carboxy-AC-DI-SOL ® NF XVI from FMC, USA, formaldehyde casein, for example the product obtainable as ESMA-SPRENG from Edelfettwerke Schlüter, Federal Republic of Germany (cf. also B. Selmeczi and M. Liptate, Sci. Pharm. 37 (1969), 284; C.A. 72, No. 16-82941) and, preferably, crosslinked, insoluble polyvinylpyrrolidone. The properties and the preparation of crosslinked, insoluble polyvinylpyrrolidone, ie. a product which is no longer water-soluble but only water-swellable, and which is also referred to as crospovidone, are described in detail in German Laid-Open Application DOS 2,255,263 of BASF Aktiengesellschaft (1974); H. F. Kauffmann & J. W. Breitenbach, Angew. Makromol. Chem. 45 (1975), 167–75; J. W. Breitenbach, Proceedings of 1967 IUPAC Symposium on Macromolecular Chemistry in Budapest, pages 529–44; and J. W. Breitenbach, H. F. Kauffmann & G. Zwilling, Makromol. Chem. 177 (1976) 2787–92. These publications are therefore incorporated by reference.

Regarding the physiocochemical properties, reference may be made to the USP Monograph. Important criteria are the hydration capacity of 4–7 (S. Kornblum & S. Stoopak, J. Pharm. Sci. 62 (1967), 43–49) and the following particle size distributions: not more than 1% larger than 250 μm and not less than 30% larger than 50 μm.

The novel intimate mixtures of the components (A), (B), and (C) are prepared by a conventional method, for example spray granulation, wet granulation or, preferably, spray drying.

The spray granulation procedure is carried out, for example, as follows: a mixture of lactose and component (C) is initially taken and sprayed with a solution of component (B) in a fluidized bed at slightly elevated temperatures, eg. from 40 to 60° C., and a dry product is obtained.

In wet granulation, for example, the lactose powder is premixed with component (C) in a suitable mixer, the solution of component (B) is poured in with further stirring, and the moist material is passed through a sieve and then dried.

As a rule, spray drying is carried out as follows: an aqueous suspension containing dissolved amounts of sprayed in a suitable spray apparatus countercurrent to, or cocurrent with, the dry air at elevated temperatures, for example using dry air at an inlet temperature of up to 120° C.

Using the stated methods, in particular spray drying, and starting from fine lactose powder, it is advantageous to produce a powder which has a narrow particle size distribution of, for example, from about 50 to 500 μm and in which from 60 to 70% of the particles are from 100 to 250 μm.

The novel mixtures obtained have excellent tableting properties and have, in particular, the following advantages over conventional direct tableting auxiliaries: good flow properties, good compressibility under low pressure, excellent disintegration properties coupled with great hardness and low abrasion of the tablets.

Compared with the conventional technique in which lactose is mixed with an active compound and cross-linked, insoluble polyvinylpyrrolidone, polyvinylpyrrolidone solution is sprayed on and the material is dried and tableted, it was surprising that preparing the novel intimate mixture beforehand and subsequently mixing in the active ingredient and carrying out direct tableting not only has the advantage of saving production steps for the tablet manufacturer but also gave an advantageous property profile, making it possible to use less carrier because of the better binding effect, and giving better disintegration of the tablet and better processability during pressing.

The Examples which follow describe the preparation of the novel mixtures and the production of tablets in comparison with other direct tableting auxiliaries and with the tableting procedure in which lactose is initially taken and polyvinylpyrrolidone and crosslinked polyvinylpyrrolidone are subsequently added.

EXAMPLES

| (1) | Lactose monohydrate EP, particle size <600 μm | 100 parts |
| --- | --- | --- |
|  | Crospovidone | 10 parts |
|  | Polyvinylpyrrolidone K30 (Povidone) | 3 parts |
| (2) | Lactose (as in 1) | 160 parts |
|  | Calcium hydrogen phosphate | 30 parts |
|  | Povidone K30 | 6 parts |
|  | Crospovidone | 10 parts |
| (3) | Lactose (as in 1) | 90 parts |
|  | Crospovidone | 5 parts |
|  | Povidone K30 | 5 parts |
| (4) | Lactose (as in 1) | 93.5 parts |
|  | Crospovidone | 3.5 parts |
|  | Povidone K30 | 3.0 parts |
| (5) | Lactose (as in 1) | 93.5 parts |
|  | Povidone K30 | 3.0 parts |
|  | Formaldehyde casein | 3.5 parts |
| (6) | Lactose (as in 1) | 93.5 parts |
|  | Povidone K30 | 3.0 parts |
|  | Sodium carboxymethylcellulose | 3.5 parts |
| (7) | Lactose (as in 1) | 93.5 parts |
|  | Povidone K30 | 3.0 parts |
|  | Croscarmellose sodium | 3.5 parts |
| (8) | Lactose (as in 1) | 93.5 parts |
|  | Povidone K30 | 3.0 parts |
|  | Sodium carboxymethyl starch | 3.5 parts |
| (9) | Lactose (as in 1) | 93.5 parts |
|  | Gelatine | 3.0 parts |
|  | Crospovidone | 3.5 parts |
| (10) | Lactose (as in 1) | 93.5 parts |
|  | Hydroxypropylmethylcellulose | 3.0 parts |
|  | Crospovidone Type A | 3.5 parts |
| (11) | Lactose (as in 1) | 93.5 parts |
|  | Hydroxypropylmethylcellulose | 3.0 parts |
|  | Crospovidone Type B | 3.5 parts |

The above mixtures can be converted to tabletable mixtures by the following procedures.

(a) The lactose and the binder are dissolved and suspended respectively in roughly equal amounts of water. The tablet disintegrating agent is added to the suspension. The suspension prepared in this manner is passed through a corundum disk mill and then sprayed in a fluidized bed.

| Spraying conditions: | |
| --- | --- |
| Inlet air | 40–80° C. |
| Nozzle | 0.8 mm |
| Spray pressure | 2–3 bar. |

(b) The lactose is initially taken together with the tablet disintegrating agent as a dry mixture in a fluidized-bed granulator and is spray-granulated with the binder, dissolved in 10 times the amount of water, in a fluidized bed.

(c) The lactose is mixed with the tablet disintegrating agent (for example in a Diosua mixer). A solution of the tablet disintegrating agent in 3 times the amount of water is poured into the mixture, the resulting mixture is mixed thoroughly for 5 minutes and then passed through a 0.8 mm sieve, and the product obtained is dried at 40° C. and then passed through a 0.5 mm sieve.

The stated methods give direct tableting auxiliaries having a flow of less than 50 seconds, measured in a Ford cup with orifice 5, and the following particle size distribution:

not more than 5% <50 μm
not more than 70% <200 μm
not less than 95% <400 μm
not more than 1% <500 μm.

EXAMPLES OF TABLETING (A) Mixture 4 obtained by method (b):99.5 parts
Lubricant:

The components are mixed for 5 minutes and the mixture is then processed on a rotary tableting machine to give biplanar tablets weighing 500 mg and having a diameter of 12 mm and moderate compressive strength. The resulting tablets have a hardness of 100N and a disintegration rate of 2–3 min.

If this test is carried out using Examples 5 to 10, the following results are obtained:

| Mixture of Example | Hardness | Disintegration rate |
| --- | --- | --- |
| 5 | 65N | 4 minutes |
| 6 | 67N | 3 minutes |
| 7 | 54N | 2–3 minutes |
| 8 | 57N | 3–4 minutes |
| 9 | 58N | 3–4 minutes |
| 10 | 36N | 4 minutes |
| 11 | 44N | 15 minutes |

(B) Paracetamol:30 parts
Mixture 4, method (b):70 parts
Magnesium stearate:0.5 parts Processing is carried out as described in Example A, and the following results are obtained:
Hardness: 70N
Disintegration rate: 1 min.
(C) Phenacetin: 30 parts
Mixture 4, method (b): 70 parts
Magnesium stearate: 0.5 parts
Processing is carried out as described in Example A, and the following results are obtained:
Hardness: 110N
Disintegration rate: 5 min.
(D) Mixture 4, method (b): 100 parts
Ascorbic acid powder: 50 parts
Magnesium stearate: 1 part
Processing is carried out as described in Example A, and the following results are obtained:
Hardness: 80N
Disintegration rate: 2 min.

I claim:

1. A direct tableting auxiliary consisting essentially of an intimate mixture of
   (A) from 88 to 96% by weight of a pulverulent carrier pharmaceutically acceptable for use in the preparation of tablets, said carrier consisting of lactose, or an amount of lactose together with not more than the same amount of mannitol or calcium phosphate as another carrier,
   (B) from 2 to 6% by weight of a binder selected from the group consisting of polyvinylpyrrolidone having a K value of from 20 to 40, hydroxypropylmethylcellulose, hydroxypropylcellulose and gelatine and
   (C) from 2 to 10% by weight of tablet disintegrating agent selected from the group consisting of crosslinked, insoluble polyvinylpyrrolidone, crosslinked carboxymethylcellulose, crosslinked carboxylmethyl starch and formaldehyde casein, all percentages being based on the direct tableting auxiliary,
   said auxiliary having a particle size distribution of from about 50 to 500 μm.

2. The direct tableting auxiliary of claim 1, wherein the binder B is polyvinylpyrrolidone having a K value of from 20 to 40.

3. The direct tableting auxiliary of claim 1, wherein the tablet disintegrating agent C is crosslinked insoluble polyvinylpyrrolidone.

4. The direct tableting auxiliary of claim 1 which contains from 2 to 5% of polyvinylpyrrolidone having a K value of 20 to 40 as the binder B and from 3 to 6% of crosslinked insoluble polyvinylpyrrolidone as the tablet disintegreting agent C.

5. A direct tableting auxiliary consisting essentially of an intimate mixture of
   (A) from 88 to 96% by weight of a pulverulent carrier pharmaceutically acceptable for use in the preparation of tablets, said carrier consisting of lactose, or an amount of lactose together with not more than the same amount of mannitol or calcium phosphate as another carrier,
   (B) from 2 to 6% by weight of a binder selected from the group consisting of polyvinylpyrrolidone having a K value of 20 to 40, hydroxypropylmethylcellulose, hydroxypropylcellulose and gelatine and
   (C) from 2 10% by weight of tablet distinge-disintegrating agent selected from the group consisting of crosslinked insoluble polyvinylpyrrolidone, crosslinked carboxymethylcellulose, crosslinked carboxymethyl starch and formaldehyde casein, all percentages being based on the direct tableting auxiliary,
   said direct tableting auxiliary being prepared by spray granulation, wet granulation or spray drying a mixture of components A, B and C.

6. The direct tableting auxiliary of claim 5, wherein the binder B is polyvinylpyrrolidone having a K value of from 20 to 40.

7. The direct tableting auxiliary of claim 5, wherein the tablet disintegrating agent C is crosslinked insoluble polyvinyl pyrrolidone.

8. The direct tableting auxiliary of claim 5, which has a particle size distribution of from 50 μm to 500 μm.

9. The direct tableting auxiliary of claim 5, prepared by spray granulation wherein a dry mixture of component A and component C is spray granulated with a solution of component B in a fluidized bed.

10. The direct tableting auxiliary of claim 5, prepared by wet granulation wherein a dry mixture of component A and component C is mixed with a solution of component B and the resulting wet mixture of components A, B and C are passed through at least one sieve and then dried.

11. The direct tableting auxiliary of claim 5, prepared by spray drying wherein components A and B are dissolved and suspended in an aqueous solution, component C is added to the suspension of components A and B and the resulting suspension or components A, B and C are spray dried.

12. A pharmaceutical tablet comprising a pharmaceutically active ingredient and the direct tableting auxiliary of claim 5.

13. A process for preparing a direct tableting auxiliary comprising spray drying, spray granulation or wet granulation of an intimate mixture consisting essentially of
   (A) from 88 to 96% by weight of a pulverulent carrier pharmaceutically acceptable for use in the preparation of tablets, said carrier consisting of lactose, or an amount of lactose together with not more than the same amount of mannitol or calcium phosphate as another carrier,
   (B) from 2 6% by weight of a binder selected from the group consisting of polyvinylpyrrolidone having a K value of 20 to 40, hydroxypropylmethylcellulose, hydroxypropylcellulose and gelatine and
   (C) from 2 to 10% by weight of tablet distintegrating agent selected from the group consisting of crosslinked insoluble polyvinylpyrrolidone, crosslinked carboxymethylcellulose, crosslinked carboxymethyl starch and formaldehyde casein, all percentages being based on the direct tableting auxiliary.

14. The process of claim 13, wherein a dry mixture of component A and component C is spray granulated with a solution of component B in a fluidized bed.

15. The process of claim 13, wherein a dry mixture of component A and component C is mixed with a solution of component B and the resulting wet mixture of components A, B and C are passed through at least one sieve and then dried.

16. The process of claim 13, wherein components A and B are dissolved and suspended in an aqueous solution, component C is added to the suspension of components A and B and the resulting suspension of components A, B and C are spray dried.

* * * * *

UNITED STATES PATENT AND TRADEMARK OFFICE
CERTIFICATE OF CORRECTION

PATENT NO. : 5,006,345
DATED : Apr. 9, 1991
INVENTOR(S) : Siegfried LANG It is certified that error appears in the above-identified patent and that said Letters Patent is hereby corrected as shown below:

In Claim 5, Col. 5, Lines 65-66:

The part reading "from 2 10% by weight of tablet distinge-disintegrating agent"
should read -- from 2 to 10% by weight of tablet disintegrating agent --

Signed and Sealed this

Sixth Day of October, 1992

Attest:

DOUGLAS B. COMER

*Attesting Officer*  *Acting Commissioner of Patents and Trademarks*